(12) United States Patent
Yang

(10) Patent No.: US 9,452,320 B2
(45) Date of Patent: Sep. 27, 2016

(54) AUTOMATIC SYSTEM AND METHOD TO CONTROL EXERCISE MACHINES

(71) Applicant: Jie Yang, North Salem, NY (US)

(72) Inventor: Jie Yang, North Salem, NY (US)

(*) Notice: Subject to any disclaimer, the term of this patent is extended or adjusted under 35 U.S.C. 154(b) by 102 days.

(21) Appl. No.: 14/535,321

(22) Filed: Nov. 7, 2014

(65) Prior Publication Data

US 2016/0129311 A1 May 12, 2016

(51) Int. Cl.
*A63B 24/00* (2006.01)

(52) U.S. Cl.
CPC ........ *A63B 24/0075* (2013.01); *A63B 24/0062* (2013.01)

(58) Field of Classification Search
CPC .............. A63B 24/00; A63B 24/0062; A63B 24/0059; A63B 71/06; A63B 24/0075; A61B 5/6898; A61B 5/1038
See application file for complete search history.

(56) References Cited

U.S. PATENT DOCUMENTS

| | | | | |
|---|---|---|---|---|
| 8,610,582 B2* | 12/2013 | Jeon | ....................... | A63B 71/06 340/5.32 |
| 9,254,416 B2* | 2/2016 | Ashby | .................... | A63B 24/00 |
| 2016/0007885 A1* | 1/2016 | Basta | ................... | A61B 5/1038 482/5 |
| 2016/0066835 A1* | 3/2016 | He | ....................... | A61B 5/6898 482/4 |
| 2016/0089569 A1* | 3/2016 | Blahnik | ............. | A63B 24/0059 434/247 |

* cited by examiner

*Primary Examiner* — Glenn Richman
(74) *Attorney, Agent, or Firm* — Mestechkin Law Group P.C.

(57) ABSTRACT

Method and system for operating a fitness exercise equipment are provided. In a preferred embodiment of the present disclosure, a system for operating a fitness exercise equipment comprises a processor and a memory device electronically coupled to the processor, the memory device storing instructions which, when executed by the processor, direct the processor to acquire an initial exercise parameters entered by a user, determine an initial exercise program based on the initial exercise parameters, and initiate movement of the fitness exercise equipment in correspondence with the initial exercise program, where the instruction to acquire the initial exercise parameters comprises instructions to detect commands entered by the user via built-in touch screen of the fitness exercise equipment, wherein instructions to detect commands entered by the user via built-in touch screen comprises detecting a curve drawn by the user on the built-in touch screen.

15 Claims, 7 Drawing Sheets

AUTOMATIC SYSTEM AND METHOD TO CONTROL EXERCISE MACHINES

CROSS-REFERENCE TO RELATED APPLICATION

This application claims the benefit of U.S. Provisional Application No. 61/902,221, filed Nov. 9, 2013.

FIELD OF THE INVENTION

The present invention pertains to a touch-screen based control and data processing system. More particularly, this invention relates to a touch-screen based automatic control system and methods which allow to program a customized cardiovascular exercise routine on exercise machines, such as treadmills, steppers, elliptical machines or stationary bikes.

BACKGROUND OF THE INVENTION

People all over the world use cardiovascular exercise equipment such as treadmills, stationary bikes, elliptical machines and steppers to improve their health and increase their fitness level. However, the more people use exercise machine, the more demands they have to satisfy their particular fitness goals. Nowadays exercise machines do not provide sufficient customization of the exercise. The person exercising on the machine only has limited choices of exercise routines.

Typically, the interface of cardiovascular exercise equipment has poor graphical presentation and format. Usually the input screen is made of a series of LED lights and has a lot of buttons. The graphical interface can merely show different exercise parameters in a real time manner. This is uninteresting and does not offer a visually stimulating experience, thus discouraging people from engaging in sports.

The state of the art, prior to the present invention, cannot be said to be "user friendly." Many people easily get bored while exercising using embedded exercise programs on exercise machines. That leads to the fact that people do not exercise as much because it is not as much fun as other things.

BRIEF SUMMARY OF THE INVENTION

The invention disclosed comprises an automatic control system and method for creating a personalized routine to use on exercise machines such as treadmills, stationary bikes, elliptical machines and steppers, commonly used for stationary cardiovascular exercise. It utilizes the touch screen technology and allows user to customize the exercise program and save it to the exercise machine or the external memory stick. The person exercising is fully entitled to modify the program at any time. This allows a user to adjust various parameters, thus improving and enriching workout experience.

BRIEF DESCRIPTION OF THE DRAWINGS

Some embodiments of the present invention are illustrated as an example and are not limited by the figures of the accompanying drawings, which are as follows.

DETAILED DESCRIPTION OF THE INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

New devices and systems are discussed herein. In the following description, for purposes of explanation, numerous specific details are set forth in order to provide a thorough understanding of the present invention. It will be evident, however, to one skilled in the art that the present invention may be practiced without these specific details.

The present invention will now be described by referencing the appended figures representing preferred embodiments.

Figure 1:
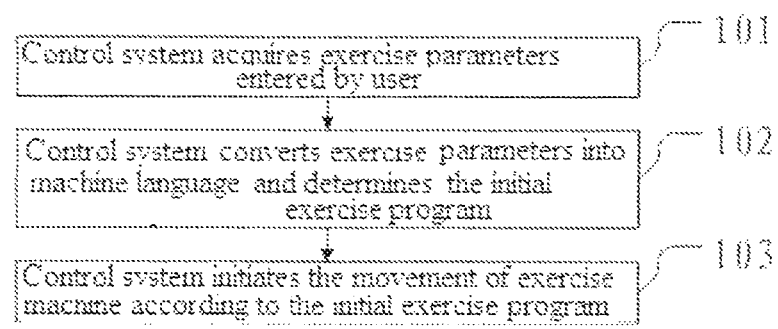
FIG. 1 is a flowchart of the first embodiment.

As shown on FIG. 1, the invention provides an automatic control for creating a personalized routine to use on exercise equipment such as treadmills, stationary bikes, elliptical machines and steppers. The method is implemented through the following steps:

Step 101, the control system acquires the customized exercise parameters entered by user;

In the embodiment, there are tour methods to acquire the customized exercise parameters entered by user.

$1^{st}$ method: control system acquires the customized exercise parameters entered by user on the keyboard.

$2^{nd}$ method: control system acquires the customized exercise parameters entered by user on the built-in touch screen.

3rd method: control system acquires the customized exercise parameters through a curve drawn by user on the built-in touch screen.

4th method: control system acquires the customized exercise parameters through coordinate values entered by user on the built-in touch screen.

Wherein, the customized exercise parameters include: the calories per minute or total calories, exercise time, speed, distance, instantaneous incline, power, etc.

Additionally, the exercise machine will generate an alert message when entered customized exercise parameters exceed the maximum set value. For example, if the speed entered by the user is more than 24 km/h, which exceeds the range of the 0-24 km/h on an exercise machine, the calculated incline value will exceed the range of −3%-15%, which will trigger an alert.

Step 102, the control system converts the customized exercise parameters into machine language, determining the initial exercise program;

The initial exercise program may be: Constant calories per minute, Total constant calories, Manual program or Pre-program.

When the initial exercise program is the Manual program, the customized exercise parameters may be acquired through all four above-described methods. For example, the exercise machine will acquire the customized exercise parameters and determine the Manual program based on the curve or the coordinate values entered in the control area on the built-in touch screen.

When the exercise program is Constant calories per minute or Total constant calories, the exercise machine will acquire the exercise parameters based on the parameters entered by user and the corresponding formula and will determine the program correspondingly.

The formula for calories per minute in this embodiment is $Z=aX+bY+c$, and there are no restrictions in terms of the specific values for the exercise parameters such as X, Y and Z. The different definitions as well as the values for X, Y and Z can result in the same exercise effect. The energy is calculated in calories.

When the initial exercise program is the Pre-program, the exercise machine will move according to the pre-saved exercise program selected by user on touch screen or keyboard from the pre-saved program list. The Pre-program is either pre-saved in the system by manufacturers or designed and saved by user.

Also, the exercise machine will display the graphic information reflecting the initial exercise program so that the user could track the exercise progress.

Step 103, control system initiates the movement of exercise machine according to the initial exercise program.

When the control system initiates the movement of the exercise machine according to the initial exercise program, a tracking mark will be generated on the screen to indicate the real time exercise status.

If the user wants to change the current exercise parameters, he/she may enter the corresponding changes on the built-in touch screen or keyboard and the exercise system will replace the initial exercise program with another exercise program (Second exercise program) according to the updated values, wherein the Second exercise program can be Manual program, Constant calories per minute. Total constant calories or Pre-program.

It needs to be noted that a safety warning message will be generated to prompt the user to modify the entered data if the entered exercise parameter exceeds the maximum set value.

Figure 2:
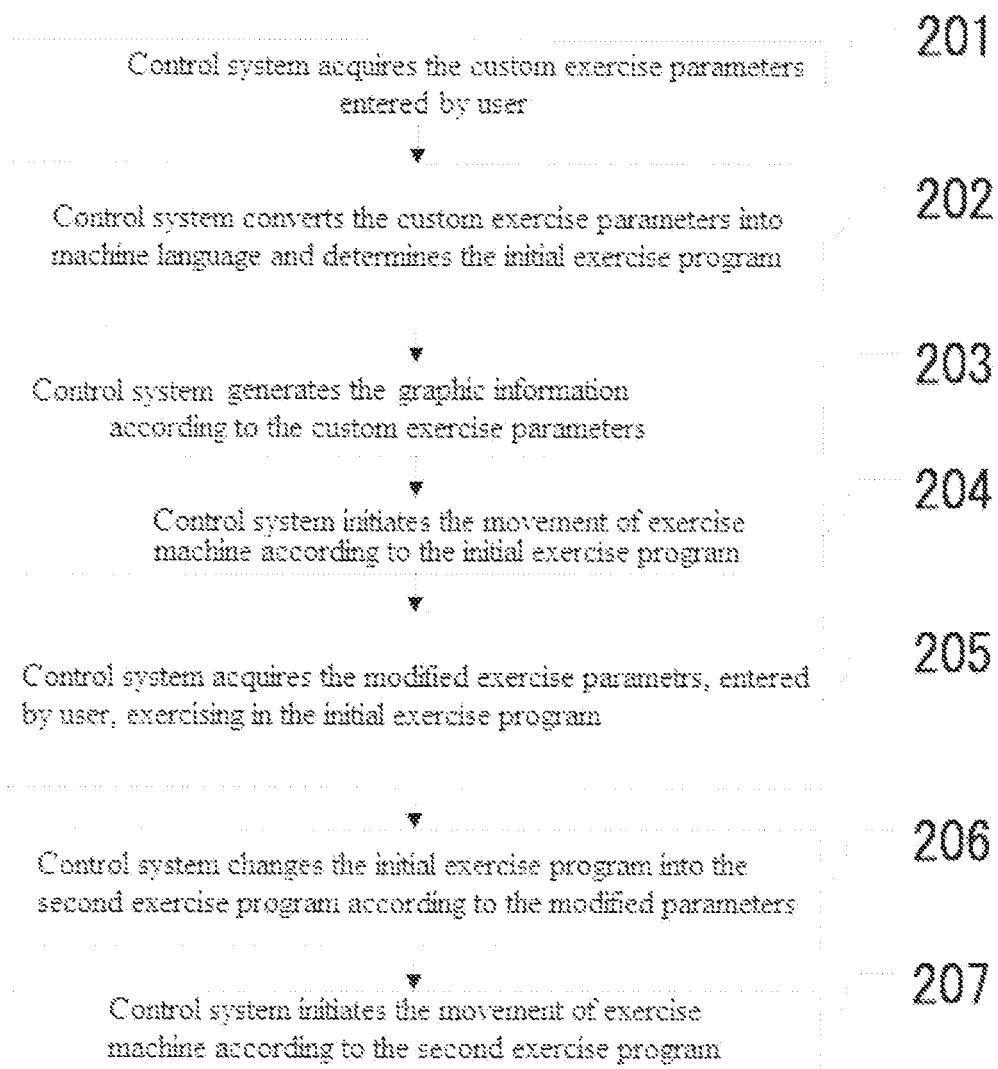
FIG. 2 is a flowchart of the second embodiment.

As shown on FIG. 2, the invention provides another automatic control method which includes the following steps:

Step 201, the control system acquires the customized exercise parameters entered by user;

Wherein, there are two methods to acquire the customized exercise parameters entered by user;

1st method: the control system acquires the customized exercise parameters entered by user on the keyboard.

2nd method: the control system acquires the customized exercise parameters entered by user on the built-in touch screen.

Wherein, the exercise parameters include: the calories per minute or total calories, exercise time, speed, distance, instantaneous incline, power, etc. This control system may be used on any exercise machine such as exercise treadmill, elliptical machine, stepper, stationary bike, etc.

Figure 3:
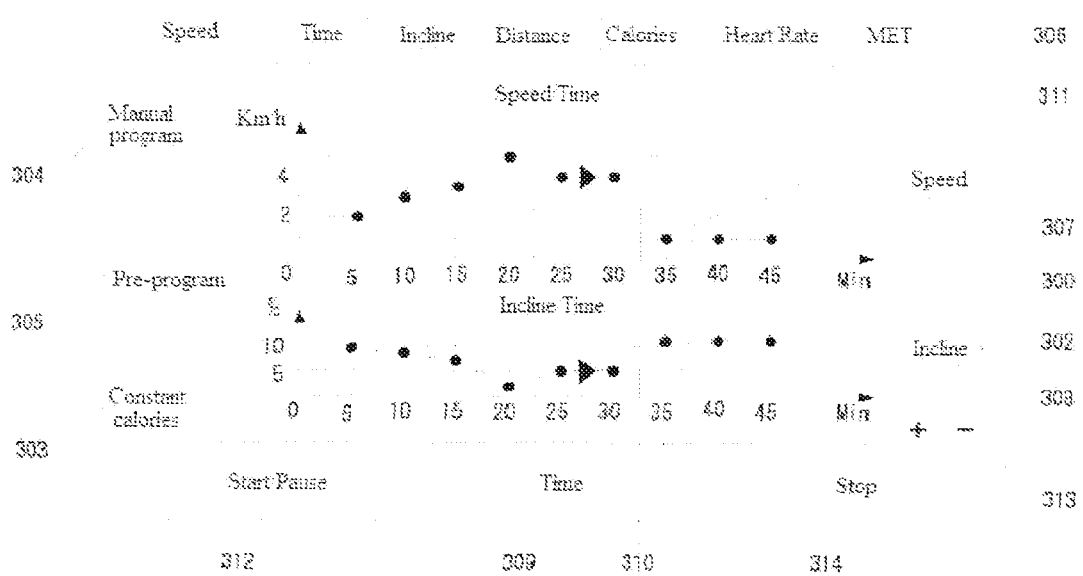
FIG. 3 represents a display of the invention.

As shown on FIG. 3, Customized Exercise Parameters 301 is displayed on top of the Display 300. The user may enter the corresponding parameters in Customized Exercise Parameters 301 after selecting the exercise time on the time axis. For example, the user can enter speed 5 km/h in 301 and chose 1 min time interval on the time axis, enter the speed 8 km/h and chose 2 min time interval, enter 20 km/h and chose 30 min time interval. Additionally, if there is only one exercise parameter entered in 301 and no time is selected on the time axis, the control system will implement the exercise program at the constant speed for the whole duration of the workout.

When the Customized Exercise Parameters 301 are displayed as unchangeable numbers, (displayed in LCD), it means that these parameters are the current exercise parameters, such as calories, exercise time, speed, distance, instantaneous incline and power, etc. The user can also enter the exercise parameters by clicking on the coordinate axis. For example, the user may click on the coordinate (1 min, 5 Km/h), (2 min, 8 Km/h) and (30 min, 20 Km/h) at the time/speed axis to customize the program. Similarly, if there is only one coordinate value, the control system will implement the exercise program at the constant speed during the whole duration of the workout.

In the embodiment. Display 300 shown on FIG. 3 is just one of the display methods. There are no restrictions in the displaying methods. For the convenience of description, Display 300 on FIG. 3 will be described as an example.

It needs to be mentioned that the user can click Constant Calories Program button 303 located on Display 300 and enter corresponding customized exercise parameters on the time axis when he/she wants to exercise in the Constant calories per minute or Total constant calories programs. If the user wants to exercise in Manual program, he/she can click the Manual Program button 304 located on Display 300 and then enter the desired exercise parameters on the time axis. If the user wants to exercise in Pre-program, he/she can click the Pre-program button 305 located on Display 300 and then select the desired exercise program from the list; the exercise programs in the list were uploaded by manufacturer or previously saved by user. For example, after the user clicks on the button 305 located on the Display 300 as shown on FIG. 3, all exercise programs saved on the machine will be displayed on the Display 300, and then the user can select the desired program.

Additionally, if new exercise parameters exceed the maximum value, an alert message will be generated to prompt the user to change the parameter.

Optionally, the exercise machine may produce a sound to indicate if the user enters the customized exercise parameter on touch screen successfully. For example, the exercise machine will makes a sound of "poom" after successful acquisition of the customized exercise parameter entered by user on touch screen. Otherwise it makes a sound of "pow".

Step 202, control system converts the customized exercise parameters into machine language which determines the initial exercise program;

When the initial exercise program is Manual program, the control system will generate the Manual program according to the entered exercise parameters. The Manual program is the exercise program designed by the user; it has no energy or time restrictions. The control system will define the program based on the exercise parameters, obtained through the curve drawn by user or coordinates selected by user.

When the initial exercise program is Constant calories per minute, the control system will obtain the exercise parameters according to the entered parameters and the corresponding formula and will then define the exercise program. Exercise in Constant calories per minute program is the exercise where the calories per minute calculated by the control system are equivalent to the calories entered by the user.

We will use treadmill as an example. When the initial exercise program is the Constant calories per minute, the exercise machine will calculate the speed or instantaneous incline using the formulas $$X = \frac{Z - bY - c}{a} \text{ or } Y = \frac{Z - aX - c}{b}$$

correspondingly, wherein the X represents the minute speed, Y represents the minute incline, Z represents the minute calories burnt, a & b are coefficients, and c is constant number, where a=0.05* Bodyweight in kg, b=0.225* Bodyweight in kg and c=3.5* Bodyweight in kg. Then the control system will generate the Constant calories per minute program according to the exercise parameters X and Y.

For example, when a user weighing 150 kg wants to exercise in Constant calories per minute, he/she should enter the calories Z which he/she wants to burn each minute (for example, the user enters 0.4 calorie/min in the dialog box) and then enter exercise parameters on the coordinate axis. In order to ensure that Z is 0.4 calorie/min, when the user enters 20 Km/h on the speed axis and 1 min on the time axis, the exercise machine will automatically acquire a=7.5, b=33.75 and c=525 using the above-mentioned formula and determine Y=2.2%/min to get the coordinate (1 min, 2.2%) on the coordinate axis of ineline/time. Similarly, if the user chooses the time on the time axis and enter the correlated exercise parameter, the control system will calculate other corresponding exercise parameters. A line will be generated automatically between two closest coordinate values in the same coordinate axis and the coordinates covered by this line will be calculated in the same way as the coordinates entered by user. Ail the exercise parameters obtained are used to define the Constant calories per minute program and generate graphic information displayed on the exercise machine screen.

When the initial exercise program is the Total constant calories, the control system will calculate the total calories burnt each minute based on the formula Z=aX+bY+c and sum them up. The Total constant calories exercise is the exercise where the total calories calculated by the control system are equivalent to the total calories entered by the user.

This program has some restrictions to ensure that the total calories calculated by the control system are equivalent to the calories entered by user.

For example, when a user weighing 150 kg wants to exercise in the Total constant calories, he/she should enter the total constant calories Z in the dialog box and the customized exercise parameters on the coordinate axis. After the user enters the customized exercise parameters, the exercise machine will calculate all the single minute calories burnt according to formula Z=aX+bY+c and sum them up. Once the calculated calories of the programmed exercise at the time point "T" reach the amount of calories entered by user in Total constant calories program, user will not be able to continue programming beyond the time point "T".

There are no restrictions in terms of the specific values for the exercise parameters such as X, Y and Z. The different definitions as well as the values for X, Y and Z can result in the same exercise effect. The energy is calculated in calories.

If the exercise machine is elliptical machine, stepper or stationary bike, the exercise parameters will also be obtained based on the formulas for Constant calories per minute or Total constant calories.

The process of defining the initial exercise program according to the customized exercise parameters can refer to the existing technology, so it is not described in details here.

When the initial exercise program is the Pre-program, the exercise system will initiate the movement of the exercise machine according to the exercise program selected by user on touch screen or on keyboard from the list of stored programs, arranged in a certain order (alphabetically or based on different parameters, such as speed, the instantaneous slope and the calories per minute). Pre-programs are either default exercises, programmed by the manufacturer or the exercises saved by users. When the user selects the pre-program, the exercise machine starts to move after the user clicks on the Storage button 305 on Display 300 and selects one of the exercise programs. The user Can select the previously saved exercise program on Display 300 by its name and time when it was saved.

Step 203, the control system generates the graphic information based on the customized exercise parameters;

More specifically, the control system generates graphic information based on the exercise parameters entered by user to provide a graphic image so that the user could track his/her current exercise status.

As shown on FIG. 3, after the user enters Customized Exercise Parameters 301 on the time axis (by entering coordinates or drawing a curve) on Display 300, the control system will automatically calculate other exercise parameters based on entered parameters using the corresponding formula when the initial exercise program is either the Constant calories per minute or the Total constant calories and will then generate Graphic Information 302. When the initial exercise program is the Manual program, the exercise machine will generate Graphic Information 302 based on the customized exercise parameters entered by user. When the initial exercise program is the Pre-program, the exercise machine will generate Graphic Information 302 based on the exercise program selected by user.

Step 204, control system initiates the movement of exercise machine according to the initial exercise program;

As shown on FIG. 3, the control system will add a Tracking Mark 306 on the Graphic Information 302 located on the Display 300 to indicate the real time exercise status. When Display 300 cannot show the Information 302 completely, the user can view it by moving the slide bar. When Display 300 cannot show the Graphic Information 302 completely, the user can click Zoom buttons 313 to zoom in or zoom out the Graphic Information 302 on Display 300 so that the user could see the program in details or see the entire exercise program. Graphic Information 302 will enlarge on Display 300 when the user slides two fingers in opposite direction on touch screen, when the user slides two fingers to the center Graphic Information 302 will diminish. The zoom function of the exercise machine is not limited in the embodiment.

When the user wants to pause or stop the exercise he/she can click the Stop 312 Storage button: the user will then have the option to save the program for further usage or not to save. If the user chooses not to save the program, he/she will have two options: to continue the current exercise program or start a new program (Step 201).

Step 205, the control system alters the data after the user changes the parameters in the initial exercise program;

The data modification commands include: modification of exercise parameters or addition of new exercise parameters.

If the user is not satisfied with the current exercise status at time point "T", he/she may select the corresponding areas of time point "T" and then change or add exercise parameters on keyboard or touch screen.

It needs to be noted that the customized exercise parameters in the exercise machine are correlative when the initial exercise program is the Constant calories per minute. In other words, once the exercise parameter is changed, the associated parameters will change automatically according to the formula to ensure that the calories per minute are constant. User can change any of the exercise parameters at any time.

When the initial exercise program is the Total constant calories, once the calculated calories of the customized exercise at time point "T" reach the amount of calories entered by user; user will not be able to change the customized exercise parameters behind the time point "T". Any changes of the parameter value at or before the time point T will change correlated values to ensure that calories are constant. If the total calories of customized exercise do not yet reach the total calories entered by the user, the user can still change or add exercise parameters to ensure that total calories of the customized exercise are equivalent to the entered calories. For example, the user can shorten time or change the incline.

When the initial exercise program is Manual program or Pre-program, user can choose the correlated editing areas of time point "T" or areas of different time points at the same time, and change the values by clicking the Speed 307, Incline 308 or Time 309 located on Display 300 on keyboard or touch screen. The "Up" arrow and right arrow are used to increase parameter, the "down" arrow and the left arrow are used to decrease the parameter.

Figure 5:
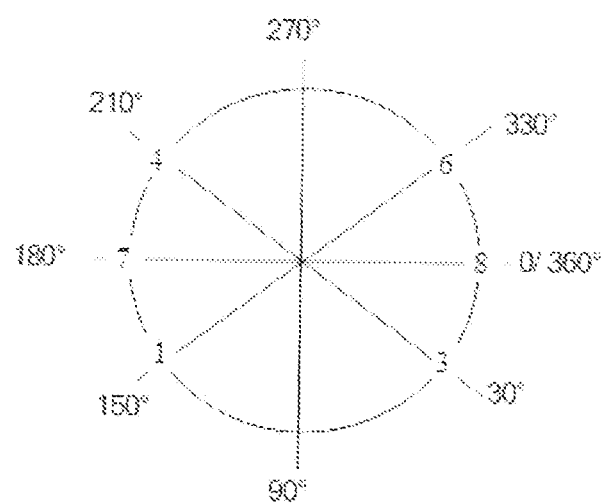
FIG. 5 is a structural diagram of touch-screen methods for the first embodiment.

Range of angles, defining directions of fingers when using a touch screen, is based on the circular angle of 0-360 degrees, as shown on FIG. 5. The finger should touch the Center 1 and then slide to the points 1-8, as follows:

Upward slide: the finger moves up from the Center 1 to the Points 1-3, equal to angles 210°-330°;

Downward slide: the finger moves down from the Center 1 to the point 4-6, equal to angles 30°-150°;

Left slide: the finger moves left from the Center 1 to the Points 1,7,4, equal to angles 150°-210°;

Right slide: the finger moves right from the Center 1 to the points 3, 8, 6, equal to angles of 330°-30°.

Wherein, upward and downward slides are used to control exercise intensity, for example, the speed/incline of the treadmill and the resistance/incline of the elliptical machine, etc. Left and right slides control the duration of exercise. Each slide will increase/decrease the parameter by 3 units (for speed 1 unit is equal to 0.1 km, for time 1 unit is equal to 1 minute). When user doesn't select the control area, the slide will change the current time variable.

When user selects the control area, the slide will change the exercise parameter. When the user toadies or clicks control area, it will start flashing. If no action was taken within a certain time (appr. 3 seconds) or the areas were not reselected, the flashing will stop to indicate that the area is unselected.

Furthermore, if the user wants to leap over from the current exercise time point "T" to any time before or alter the time point "T" (for example, time point "T+n" where "n" is any number), the user can quickly double click at the time point "T+n", and then the exercise program will start from time "T+n".

Step 206, the control system changes the initial exercise program into the second exercise program based on the parameters entered on touch screen or keyboard.

After the exercise machine acquires the modified parameters entered by user, it will recalculate the speed with formula $$X = \frac{Z - bY - c}{a}$$

or instantaneous slope with formula $$Y = \frac{Z - aX - c}{b}$$

to determine the second exercise program if the initial exercise program is the Constant calories per minute. If the initial exercise program is the Total constant calories, it will recalculate all the single minute calories with formula $Z=aX+bY+c$ and sum them up to determine the second exercise program;

When the initial exercise program is the Pre-program, the exercise machine changes the initial exercise program into the second exercise program based on the parameters entered on touch screen or keyboard. When the initial exercise program is the Manual program, the exercise machine will change it into the second exercise program based on the customized exercise parameters entered on touch screen or keyboard.

For example, a user designed a 9 minute-long exercise program, wherein the speeds for 0-3rd Min, 3rd-6th Min and 6th-7th min are 8 km/ft, 10 Km/h and 7 Km/h, respectively. When the user is exercising at the 2nd min and wants to decrease the speed of 10 km/h at $3^{rd}$-$6^{th}$ min, he/she can select the areas at the corresponding time zone and change the speed using keyboard or touch screen.

Additionally, when the new added or modified exercise parameter exceeds the maximum value, an alert message will be generated to prompt the user to change the value.

Step 207, control system initiates the movement of the exercise machine according to the second exercise program.

The control system converts the modified exercise parameters into machine language initiating the movement of the exercise machine; then the control system will generate the graphic information according to the modified exercise parameters and display the graphic information on the screen.

It needs to be noted that Step 205-207 are optional. The exercise machine will execute Steps 205-207 only after the data is changed by user. As shown on FIG. 2, the dashed boxes used for Steps 205-207 indicate that the steps are optional.

Figure 4:
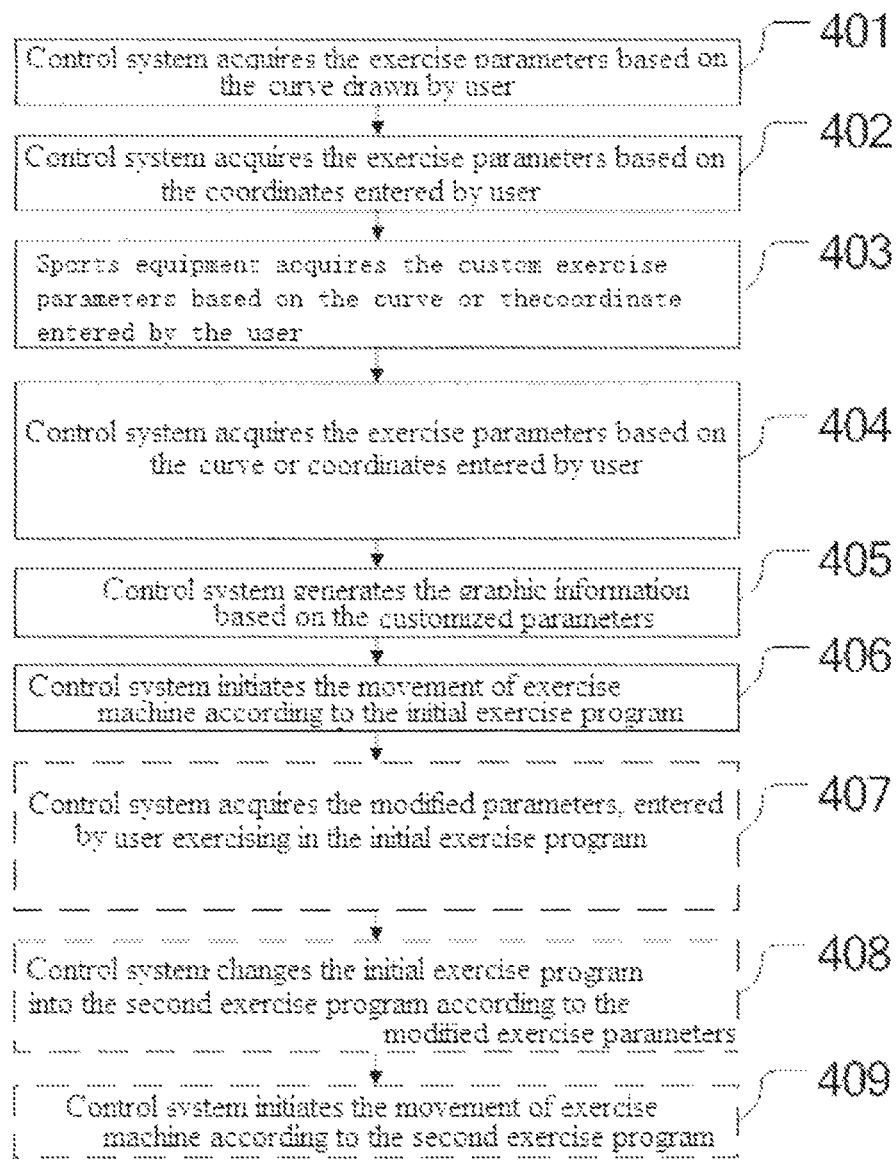
FIG. 4 is the flowchart for another automatic control method for the first embodiment.

As shown on FIG. 4, the invention provides another automatic control method which includes the following steps:

Step 401, the control system acquires information through the curve drawn by user;

As shown on FIG. 3, the user may draw Curve 310 on Display 300.

This method may be used on any exercise machine such as treadmill, elliptical machine and stationary bike, etc. The treadmill is used as an example in this embodiment.

When the new added or modified exercise parameter exceeds the maximum value, an alert message will be generated to prompt the user to change the value.

Step 402, the exercise machine acquires information through coordinates entered by user;

In the embodiment, the control system may also acquire the exercise parameters through the coordinates entered by user. As shown on FIG. 3, the user may enter Coordinate 311 on Display 300 by touching Coordinate 311. When user enters a coordinate at time point "T", the control system obtains the exercise parameter according to the entered coordinate, and then initiates the movement of the exercise machine at the constant speed in the exercise time restricted on the time axis by user. When the user enters more than one coordinate, the control system obtains all exercise parameters and initiates the corresponding movement of the exercise machine, which will be illustrated below.

When the new added or modified exercise parameter exceeds the maximum value, an alert message will be generated to prompt the user to change the value.

It needs to be noted that Step 401-402 are mutually exclusive, so they cannot be executed at the same time in the embodiment. However, if needed, the Steps 401-402 can be executed at the same time. For example, when the user enters the coordinate within the curve area, the control system will replace the parameters obtained from the curve with the parameters, entered through coordinate. When the user enters the coordinate out of the curve area, the control system will connect the coordinates and the curve.

Step 403, the control system acquires the customized exercise parameters based on the curve or the coordinates entered by user;

The exercise parameters include: the calories per minute or total calories, exercise time, speed, distance, instantaneous incline, power, etc.

Step 404, the control system converts the customized exercise parameters into machine language which defines the initial exercise program;

In this step, the initial exercise program can be the Constant calories per minute, the Total constant calories, the Manual program or the Pre-program. The process of defining the initial exercise program is described in Step 202 of FIG. 2.

Step 405, the control system generates the graphic information based on the customized exercise parameters;

Specifically, the control system generates the graphic information based on the customized parameters to provide a graphic image so that user could tract his/her exercise status.

As shown on FIG. 3, the control system will acquire Customized Exercise Parameters 301 based on the curve or coordinate entered on Display 300 to generate Graphic Information 302 when the initial exercise program is the Constant calories per minute or the Total constant calories. When the initial exercise program is the Manual program, the control system will generate Graphic Information 302 based on the customized exercise parameters entered by user. When the initial exercise program is the Pre-program, the control system will generate Graphic Information 302 based on the exercise program selected by user. Wherein, the Graphic Information 302 provides a graphic image of the current exercise status.

The control system acquires Customized Exercise Parameters 301 based on the curve or the coordinate entered by user and connects all entered parameters by dashed lines or into one continuous curve, thus generating Graphic Information 302.

Step 406, the control system initiates the movement of exercise machine according to the initial exercise program;

The detailed process is shown in Step 204 of FIG. 2.

Step 407, the control system acquires the changes made by user to the parameters in the initial exercise program;

The changes of current parameters may include modification of exercise parameters or addition of new exercise parameters.

If the user is not satisfied with the current exercise status at time point "T", he/she can select the corresponding areas of time point "T" and then change or add exercise parameters on keyboard or touch screen.

It needs to be noted that the customized exercise parameters in the exercise machine are correlative when the initial exercise program is the Constant calories per minute. In other words, once the exercise parameter is changed, the associated parameters will change automatically according to the formula to ensure that the calories per minute are constant. User can change any of the exercise parameters at any time.

When the initial exercise program is the Total constant calories, once the calculated calories of the customized exercise at time point "T" reach the amount of calories entered by user; user will not be able to change the customized exercise parameters behind the time point "T". Any changes of the parameter value at time point T will change correlated values to ensure that calories are constant. If the total calories of customized exercise do not yet reach the total calories entered by the user, the user can still change or add exercise parameters to ensure that total calories of the customized exercise are equivalent to the entered calories. For example, the user can shorten time or change the incline.

For example, as shown on FIG. 3, the user may click Speed 307, Incline 308 or Time 309 on Display 300 with keyboard or touch screen after selecting the control area at Moment T or T+n, wherein n is any positive number. The up arrow and right arrow are used to increase the parameter values while the down arrow and left arrow are used to decrease the values.

Step 408, control system changes the initial exercise program into the second exercise program based on the modified parameters entered by user;

After the exercise machine receives the modified data entered by user, it will recalculate the speed with formula $$X = \frac{Z - bY - c}{a}$$

or instantaneous slope with formula $$Y = \frac{Z - aX - c}{b}$$

to determine the second exercise program if the initial exercise program is the Constant calories per minute. If the initial exercise program is the Total constant calories, the control system will recalculate all the single minute calories with formula Z=aX+bY+c and sum them up to determine the second exercise program;

When the initial exercise program is the Pre-program, the control system changes the initial exercise program into the second exercise program based on the parameters entered on touch screen or keyboard. When the initial exercise program is the Manual program, the exercise machine will change it into the second exercise program based on the customized exercise parameters entered on touch screen or keyboard.

It can be noted that the second exercise program may be the Constant calories per minute, the Total constant calories or the Manual program.

It needs to be noted that a safety warning message will be generated to prompt the user to reenter the parameters if the modified or added customized exercise parameters exceed the maximum set value.

Step 409, the control system will initiate the movement of the exercise machine according to the second exercise program.

Specifically, the control system converts the customized exercise parameters modified by user into machine language initiating the movement of the exercise machine and generating the corresponding graphic information on the display.

It needs to be noted that Steps 407-409 are optional. The control system executes Steps 407-409 after receiving the modified parameters entered by user. On FIG. 4, the dashed box indicates that Steps 407-409 are optional.

Figure 6:
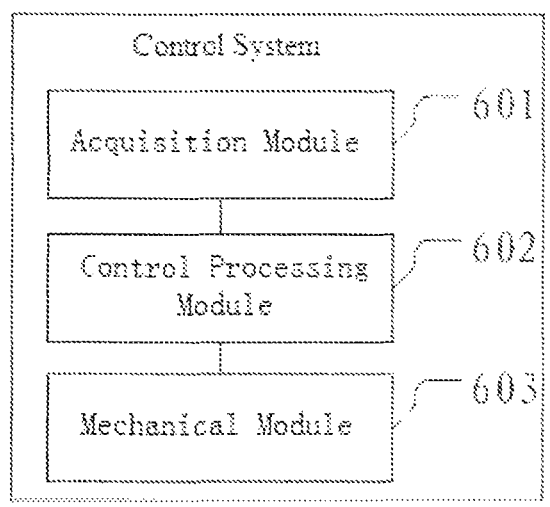
FIG. 6 represents a general structure of the invention.

As shown on FIG. 6, the control system in another embodiment includes: Acquisition Module 601, Control Processing Module 602 and Mechanical module 603. This system may be used on any exercise machine such as treadmill, elliptical machine and stationary bike, etc.

Acquisition Module 601 is used to acquire the customized exercise parameters entered by user and to transfer them to Control Processing Module 602;

Control Processing Module 602 is used to convert the customized exercise parameters received by Acquisition Module 601 into machine language, which defines the initial exercise program, and to transfer the program to Mechanical Module 603;

Mechanical Module 603 is used to receive the initial exercise program defined by Control Processing Module 603 to initiate the movement of the exercise machine.

Figure 7:
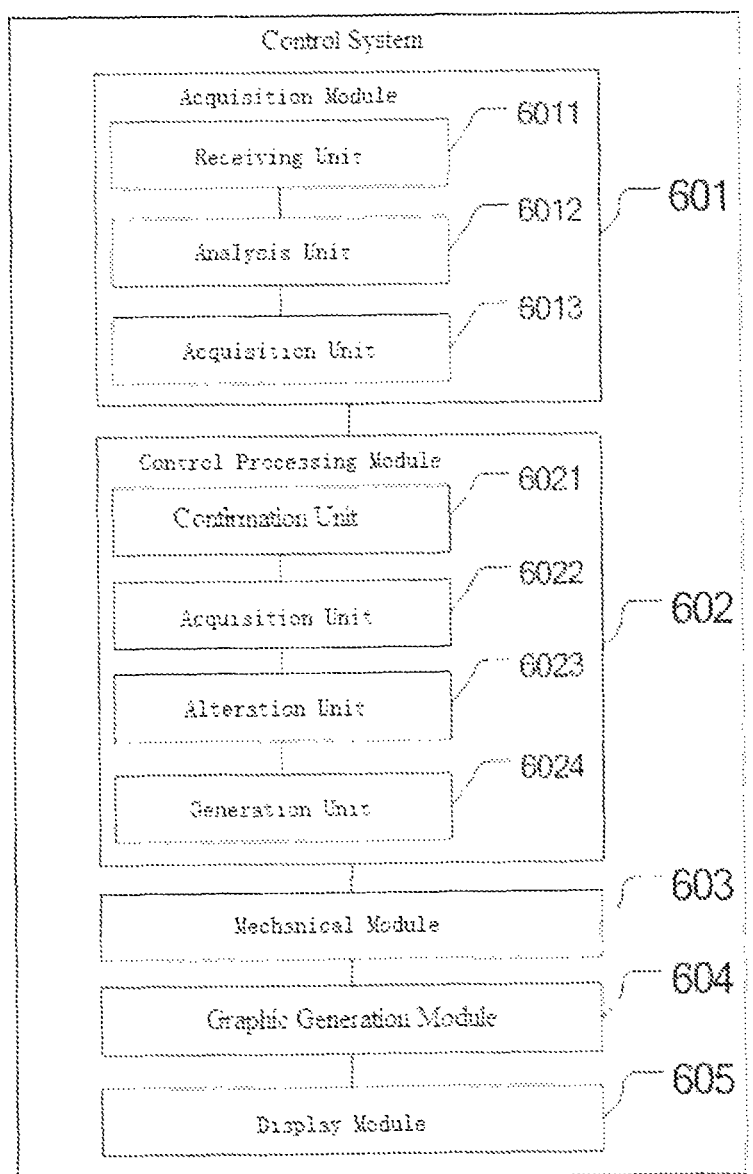
FIG. 7 represents a detailed structure of the invention

FIG. 7 shows that there are four different methods through which the Acquisition Module 601 may obtain the exercise parameters entered by user: Acquisition Module 601 consists of Receiving Unit 6011, Analysis Unit 6012 and Acquisition Unit 6013.

$1^{st}$ method: Receiving Unit 6011 acquires the customized exercise parameters entered by user on keyboard;

$2^{nd}$ method: Receiving Unit 6011 acquires the customized exercise parameters entered by user on touch screen.

$3^{rd}$ method: Receiving Unit 6011 receives the curve drawn by user on touch screen and Analysis Unit 6012 analyzes the curve to obtain customized exercise parameters.

$4^{th}$ method: Receiving Unit 6011 receives the coordinates entered by user on touch screen and Acquisition Unit 6013 acquires the customized exercise parameters based on the corresponding coordinate.

The exercise parameters include: the calories per minute or total calories, exercise time, speed, distance, instantaneous incline, power, etc.

In addition, Receiving Unit 6011 acquires the commands entered by user on touch screen or keyboard. The commands initiate the movement of exercise machine according to the Pre-program stored in the system.

The system also contains Graphic Generation Module 604 and Display Module 605;

After Acquisition Module 601 acquires the customized exercise parameters, Graphic Generation Module 604 generates the graphic information based on the customized exercise parameters to provide user with the graphic image of the current exercise status information on Display Module 605. It needs to be noted that Module 604 can receive the customized exercise parameters sent by Acquisition Module 601 or Control Processing Module 602.

Furthermore, Control Processing Module 602 consists of Confirmation unit 6021, Acquisition Unit 6022, Alteration Unit 6023 and Generation Unit 6024;

We take treadmill as an example. When the initial exercise program is Manual program, the Confirmation unit 6021 will confirm the Manual program according to exercise parameters obtained by the Acquisition Module 601. The Manual program is the exercise program customized by user, wherein the exercise parameters were chosen by user. When the initial exercise program is either Constant calories per minute or Total constant calories, the exercise control system will define the exercise program according to the parameters entered by user and the corresponding calories formula to ensure that calorie expenditure is constant.

When the initial exercise program is the Constant calories per minute, Acquisition Unit 6022 will obtain the corresponding minute speed or minute incline value according to the formula $$X = \frac{Z - bY - c}{a}$$

or $$Y = \frac{Z - aX - c}{b},$$

wherein the X represents the minute speed, Y represents the minute incline, Z represents the calories burnt per minute, a&b are coefficients, and c is constant number. In which, a=0.05* Bodyweight in kg, b=0.225* Bodyweight in kg, c=3.5* Bodyweight in kg. Confirmation Unit 6021 determines the values for constant calories per minute based on the customized exercise parameter X or Y. The Constant calories per minute exercise is the exercise wherein the calories which should be burnt per minute calculated by system is equivalent to the calories entered by the user.

When the initial exercise program is the Total constant calories, Acquisition Unit 6022 will obtain all the calories calculated for every minute based on the formula $Z=aX+bY+c$, and sum them up. The Total constant calories exercise is the exercise wherein the total calories calculated by the system are equivalent to the calories entered by the user.

When the initial exercise program is the Pre-program, the Confirmation unit 6021 will obtain the exercise parameters based on the exercise program selected by user on touch screen or keyboard from the list of stored programs listed.

When Mechanical Module 603 initiates movement in the initial exercise program, Graphic Generation Module 604 will add a tracking mark on the Display module 605 to indicate the current exercise status.

Furthermore, when the user is not satisfied with the current exercise status, he/she can make changes to the commands to Receiving Unit 6011 in Acquisition Module 601, then the Receiving unit 6011 will transfer the modified commands to the Alteration unit 6023 located in the Control Processing module 602. Then the Alteration unit 6023 will change the initial exercise program into the Second exercise program according to the modified parameters, wherein the Second exercise program can be Manual program. Constant calories per minute, Total constant calories or Pre-program.

When the new added or modified exercise parameter exceeds the maximum value, the Generation unit 6024 will generate an alert message and transfer it to Display module 605 to prompt user to change the value.

The embodiments of the invention in which an exclusive property or privilege is claimed are defined as follows:

1. A method comprising:
   acquiring, by a control system of a fitness exercise equipment, an initial exercise parameters entered by a user, wherein acquiring the initial exercise parameters comprises detecting commands entered by the user via built-in touch screen of the fitness exercise equipment, wherein the built-in touch screen displays a coordinate axis;
   determining, by the control system of the fitness exercise equipment, an initial exercise program based on the initial exercise parameters; and
   initiating, by the control system of the fitness exercise equipment, movement of the fitness exercise equipment in correspondence with the initial exercise program.

2. The method of claim 1, wherein detecting commands entered by the user via built-in touch screen comprises detecting a curve drawn by the user on the built-in touch screen of the fitness exercise equipment.

3. The method of claim 1, wherein detecting commands entered by the user via built-in touch screen comprises detecting entry of at least one coordinate value by the user on the built-in touch screen of the fitness exercise equipment.

4. The method of claim 1, further comprising:
   generating, by the control system of the fitness exercise equipment, graphics information on the built-in touch screen.

5. The method of claim 1, further comprising:
   acquiring, by the control system of the fitness exercise equipment, a modified exercise parameters entered by the user;
   determining, by the control system of the fitness exercise equipment, a modified exercise program based on the modified exercise parameters; and
   initiating, by the control system of the fitness exercise equipment, movement of the fitness exercise equipment in correspondence with the modified exercise program.

6. The method of claim 5, wherein:
   the initial exercise parameters are in the form of the curve drawn by the user on the built-in touch screen of the fitness exercise equipment; and
   the modified exercise parameters are in the form of the entry of the least one coordinate value by the user on the built-in touch screen of the fitness exercise equipment.

7. The method of claim 5, wherein:
   the initial exercise parameters are in the form of the entry of the least one coordinate value by the user on the built-in touch screen of the fitness exercise equipment; and
   the modified exercise parameters are in the form of the curve drawn by the user on the built-in touch screen of the fitness exercise equipment.

8. An apparatus comprising:
   a processor; and
   a memory device electronically coupled to the processor, the memory device storing instructions which, when executed by the processor, direct the processor to:
   acquire an initial exercise parameters entered by a user, wherein an act to acquire the initial exercise parameters comprises an act to detect commands entered by the user via built-in touch screen of the fitness exercise equipment, wherein the built-in touch screen displays a coordinate axis;
   determine an initial exercise program based on the initial exercise parameters; and
   initiate movement of the fitness exercise equipment in correspondence with the initial exercise program.

9. The apparatus of claim 8, in which the instructions, when executed by the processor, further direct the processor to:
   generate graphics information on the built-in touch screen.

10. The apparatus of claim 8, in which the instructions, when executed by the processor, further direct the processor to:
    acquire a modified exercise parameters entered by the user;
    determine a modified exercise program based on the modified exercise parameters; and
    initiate movement of the fitness exercise equipment in correspondence with the modified exercise program.

11. The apparatus of claim 10, in which the instructions, when executed by the processor, further direct the processor to:
    generate an alert in response to determining that at least one of the initial exercise parameters or the modified exercise parameters violate technical capability of the apparatus.

12. A non-transitory computer readable medium having program instructions stored thereon, that in response to execution by a processor cause the processor to perform operations comprising:
    acquiring an initial exercise parameters entered by a user, wherein acquiring the initial exercise parameters comprises detecting commands entered by the user via built-in touch screen of the fitness exercise equipment, wherein the built-in touch screen displays a coordinate axis;
    determining an initial exercise program based on the initial exercise parameters; and initiating movement of the fitness exercise equipment in correspondence with the initial exercise program.

13. The non-transitory computer readable medium of claim 12, the operations further comprising:
generating graphics information on the built-in touch screen.

14. The non-transitory computer readable medium of claim 12, the operations further comprising:
acquiring a modified exercise parameters entered by the user;
determining a modified exercise program based on the modified exercise parameters; and
initiating movement of the fitness exercise equipment in correspondence with the modified exercise program.

15. The non-transitory computer readable medium of claim 14, the operations further comprising:
generating an alert in response to determining that at least one of the initial exercise parameters or the modified exercise parameters violate technical capability of the apparatus.

* * * * *